United States Patent [19]

Sigdell et al.

[11] 4,345,999
[45] Aug. 24, 1982

[54] APPARATUS FOR PREVENTING THE ENTRY OF AIR INTO AN ARTIFICIAL ORGAN

[75] Inventors: Jan-Erik Sigdell; Gerd Krick, both of Bad Homburg, Fed. Rep. of Germany

[73] Assignee: Dr. Eduard Fresenius, Chemisch-pharmazeutische Industrie K.G., Apparatebau K.G., Bad Homburg, Fed. Rep. of Germany

[21] Appl. No.: 191,378

[22] Filed: Sep. 29, 1980

Related U.S. Application Data

[63] Continuation-in-part of Ser. No. 29,203, Apr. 12, 1979, abandoned.

[30] Foreign Application Priority Data

Apr. 27, 1978 [DE] Fed. Rep. of Germany ....... 2818390

[51] Int. Cl.³ .................... B01D 19/00; B01D 31/00
[52] U.S. Cl. .................... 210/188; 55/185; 55/190; 55/201; 210/321.2
[58] Field of Search .................. 55/52, 159, 185, 186, 55/190, 199, 201, 36, 158; 210/120, 180, 188, 321.2, 323.2, 428, 433.2, 434, 436, 472, 539; 422/45, 48

[56] References Cited

U.S. PATENT DOCUMENTS

| | | |
|---|---|---|
| 2,277,100 | 3/1942 | Hartmann .............................. 55/201 |
| 2,597,699 | 5/1952 | Bauer ................................ 55/159 X |
| 3,308,607 | 3/1967 | Mueller ................................ 55/201 |
| 3,523,408 | 8/1970 | Rosenberg ............................ 55/159 |
| 3,525,196 | 8/1970 | Brieskorn ................................ 55/52 |
| 3,626,670 | 12/1971 | Pecker ............................ 210/321.2 |
| 3,631,654 | 1/1972 | Riely et al. ............................ 55/159 |
| 3,668,822 | 6/1972 | Mannion et al. ........................ 55/159 |
| 3,778,971 | 12/1973 | Granger et al. ........................ 55/159 |
| 3,827,561 | 8/1974 | Serfass et al. ........................ 210/180 |
| 3,849,071 | 11/1974 | Kayser .................................. 422/45 |
| 3,878,095 | 4/1975 | Frasier et al. .................... 210/96.2 X |
| 3,920,556 | 11/1975 | Bowman ........................... 210/321.2 |
| 3,946,731 | 3/1976 | Lichtenstein ..................... 210/90 X |
| 4,004,587 | 1/1977 | Jess ................................ 55/159 X |
| 4,060,485 | 11/1977 | Eaton ............................. 210/90 X |
| 4,061,031 | 12/1977 | Grimsrud ......................... 55/159 X |
| 4,102,655 | 7/1978 | Jeffery et al. ......................... 55/201 |
| 4,137,160 | 1/1979 | Ebling et al. ................... 210/188 X |
| 4,162,974 | 7/1979 | Pernic ................................. 210/120 |
| 4,190,426 | 2/1980 | Ruschke ......................... 55/159 X |

FOREIGN PATENT DOCUMENTS 452265 11/1927 Fed. Rep. of Germany ........ 55/190

OTHER PUBLICATIONS

Renal Dialysis, Whelpton, 1974, pp. 42, 43, 47 & 55.

Primary Examiner—Robert H. Spitzer
Attorney, Agent, or Firm—W. G. Fasse; D. H. Kane, Jr.

[57] ABSTRACT

Air or gas is prevented from entering into the exchange zone of an artificial organ such as an artificial kidney, dialyzer, or hemofilter. For this purpose a separating path is arranged in parallel with the artificial organ or with the exchange zone or other operative portion of the artificial organ between the liquid inflow and outflow conduits. This parallel path is provided with a high flow resistance for the liquid and with a low flow resistance for the air. Such differential flow resistance may, for example, be accomplished by apertures, gas permeable materials, and eddy chambers. The gas separating path is incorporated as an integral part of the artificial organ or as an integral part of the liquid inflow and outflow conduits. According to several embodiments, an enlargement is provided in the separating path or conduit in which the liquid may "rise and dwell" to enhance air separation before the liquid flows into the operative portion of the artificial organ.

11 Claims, 7 Drawing Figures

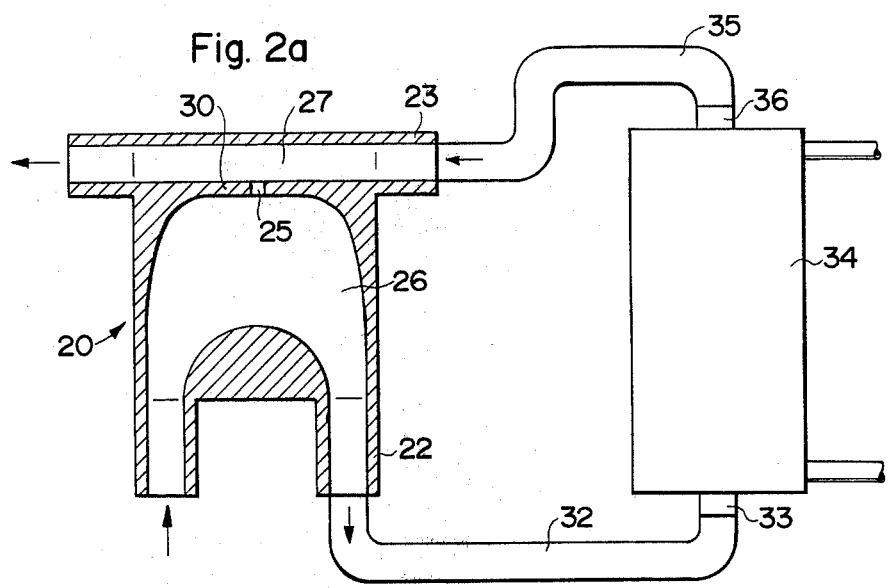
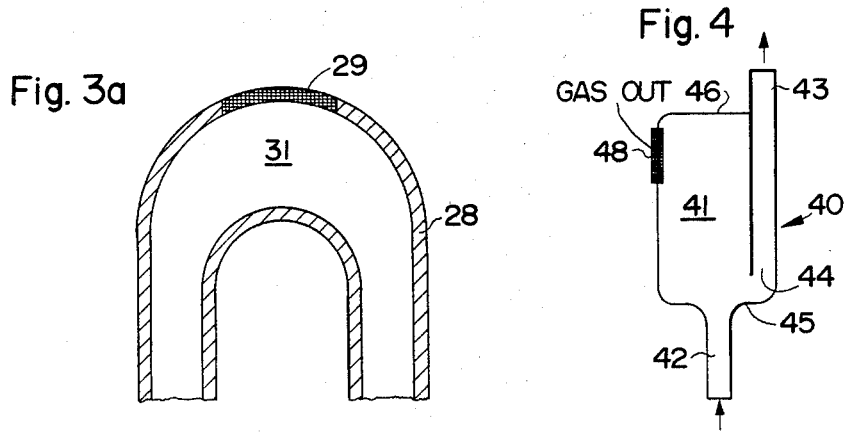
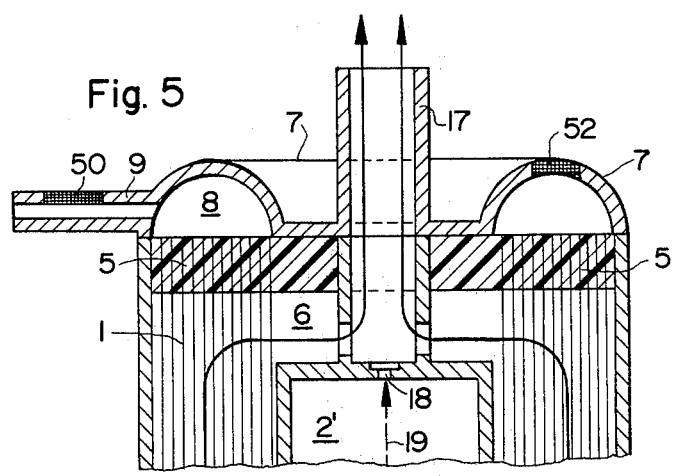

APPARATUS FOR PREVENTING THE ENTRY OF AIR INTO AN ARTIFICIAL ORGAN

CROSS REFERENCE TO RELATED APPLICATIONS

This application is a continuation-in-part of U.S. patent application Ser. No.: 029,203; filed on Apr. 12, 1979, abandoned; with the same title and common assignee. Applicants further claim as to common subject matter the priority filing date of German patent application No. P 2,818,390.6; filed on Apr. 27, 1978.

BACKGROUND OF THE INVENTION

The present invention relates to an apparatus for preventing air from entering into the operative portion of an artificial organ such as an artificial kidney, a dialyzer, a hemofilter, or an artificial liver, for example including a hemoperfusion cartridge.

During a dialysis treatment, air frequently enters the dialyzer space containing the dialysate because in the most frequent type of operation a reduced pressure is present in the space containing the dialysate. As a result, air may be drawn into such space through possible leaks or because the dialysate solution has not been degassed sufficiently.

Thus, if air enters into the dialysate containing space of the dialyzer larger air bubbles are often produced which can be removed only very slowly by dissolving the air into the degassed dialysate. Such air bubbles cover the operative surface portions of the artificial organ membrane. The efficiency of the diffusion exchange between the blood flowing on one side of the membrane and the dialysate flowing on the other side of the membrane is correspondingly impaired or diminished by such air bubbles.

Similar considerations apply when air enters into the space of the dialyzer on the side through which the blood flows similarly covering respective membrane surface areas. Another disadvantage is that air on the blood flow side increases the danger of clotting. An air bubble in the blood flow channel, for example, between the supporting grids or in a hollow fiber reduces the flow speed of the blood.

Similar difficulties may occur in a hemofilter where no dialysate is used. Rather, a fraction of the blood is caused to pass under pressure through the hemofilter membrane for separating a blood fraction by filtration.

PRIOR ART STATEMENT

The closest prior art references of which applicants are aware are the patents cited by the Examiner during prosecution of the parent application. The references are of record in the parent application and the more relevant ones are identified as follows:

| U.S. Pat. No. | Title | Inventor | Date |
|---|---|---|---|
| 4,137,160 | DEVICE FOR SEPARATING LOW DENSITY MATERIAL SUCH AS GAS BUBBLES FROM A LIQUID, AND THE USE THEREOF FOR A DIALYSIS DELIVERY SYSTEM | Ebling et al | 1979 |
| 4,162,974 | DEAERING AND RECIRCULATION SYSTEMS FOR DIALYSIS MACHINES | Pernic | 1979 |
| 3,626,670 | FLUID CIRCULATION APPARATUS INCLUDING DEAERATION AND NEGATIVE PRESSURE CONTROL | Pecker | 1971 |
| 3,827,561 | DEAERATOR FOR DIALYSIS SYSTEM | Serfass et al | 1974 |
| 3,920,556 | HEMODIALYSIS SYSTEM | Bowman | 1975 |
| 3,878,095 | DIALYSIS APPARATUS | Frazier et al | 1975 |

These patents and publications describe a variety of dialysis type machines with devices for separating air and gas from liquids used in the machines. In each case, however, the air trap or degassing apparatus constitutes a distinct and separate device or appliance not incorporated into the dialysis structure. Each device is generally of relatively large size and complexity in the order of magnitude of the dialysis machine itself. Ebling et al. employ a circumferentially swirling liquid chamber while Serfass et al describe a variety of complex arrangements for separate degassing apparatuses. Pernic provides a ball valve deairing tank. Many of the air traps such as those of Pecker and Serfass et al., Frazier et al. and Pernic employ an air space above the liquid to provide a liquid air interface which the present invention avoids. Bowman shows yet another separate degassing appliance. These references do not teach nor suggest incorporating the air trap and degassing capability directly into the internal structure of an artificial organ as contemplated by the present invention.

Most importantly, none of the above references suggests or teaches the advantage of obviating separate air traps for artificial organs thereby avoiding sterilization for reuse. The prior art devices are too elaborate and expensive for one time use. The present invention, on the other hand incorporates air separating means into the very structure of the artificial organ substantially without additional expense.

Moreover, none of the references discloses nor suggests the aspect of the present invention where the input and output conduits of the artificial organ are integrated across a common gas permeable or restrictive barrier wall so that the liquid input flow is degassed, discharging air directly into the outflow. Nor do any of these references propose to form a conduit wall itself of a differentially permeable or restrictive material for separating air from liquid as it flows in the conduit and discharging gas into the environment through the conduit wall. And finally, none of these references describes in the context of the foregoing variations of the invention the use of an enlargement in the conduit flow path or auxiliary flow path into which the liquid may rise and "dwell" before proceeding along the liquid flow path. The dwell time afforded by such enlargement of the conduit or flow path facilitates separation and removal of air before the liquid flows on to the artificial organ.

OBJECTS OF THE INVENTION

In view of the above it is the aim of the invention to achieve the following objects singly or in combination:

to provide artificial organs with a separate flow path which enables gas and air to bypass the artificial organ, to be removed prior to reaching the artificial organ, or to bypass the exchange zone or other operative portion within the artificial organ;

to arrange a parallel flow path having a differential flow resistance for different media for bypassing an artificial organ such as a dialyzer or a hemofilter or the like or the operative portions of such organ, whereby air may flow through the parallel path to a substantially larger extent than liquid;

to make the volume of the bypass as small as possible;

to assure a laminar, smooth flow in the parallel bypass, especially when used on the blood side of a dialyzer membrane to avoid blood clotting; and to provide air separating auxiliary flow path means incorporated as an integral portion of an artificial organ or as an integral portion of the liquid inflow and outflow conduits for the organ.

SUMMARY OF THE INVENTION

According to the invention an apparatus is provided for keeping air away from the active portion of an artificial organ by defining an auxiliary flow path extending in parallel with the organ or its operative portions between the liquid inflow conduits and the liquid outflow conduits. The parallel path affords a high flow resistance for the liquid and a low flow resistance relative to air or gas. Thus, air passes preferentially through the bypass, rather than the liquid. The difference in viscosity of the two media facilitates this differential response to air and liquid. However, the arrangement of apertures and/or eddy chambers increases the difference in flow resistances. Such apertures and/or eddy chambers exhibit a flow resistance which is non-linear relative to the viscosity. Thus, during normal operation when there is no gas or air present, the quantity of liquid flowing through the bypass is small and hence negligible relative to the entire dialysis flow. On the other hand, when air is present, the suitably arranged auxiliary flow path will guide the air that has entered into the system exclusively through this parallel bypass avoiding the functional region of the organ.

The parallel or bypass should, especially in the area which determines the flow resistances, have a relatively small volume in order to avoid the necessity of displacing liquid in the bypass before air can flow through the bypass in larger volume. The bypass may include apertures and/or eddy chambers, especially on the side where the dialysate flows and there is no risk of blood clotting. However, on the blood side care must be taken in the bypass that the tendency of the blood to coagulate is counteracted by a respective laminar, short flow path in the parallel connection.

The invention also contemplates providing an air separating auxiliary flow path for artificial organs where such bypass is incorporated as an integral, internal portion of the artificial organ, or as an integral part of the liquid inflow and/or outflow conduits associated with the artificial organ.

According to one form of the invention the auxiliary flow path means provides a liquid flow path in series with the artificial organ liquid inflow and outflow conduits and a gas or air flow path in parallel with such conduits delivering air and gas directly from the liquid inflow to the liquid outflow. An advantage of this arrangement is that the lower pressure at the liquid stream outflow draws gas or air through the air flow path from the liquid inflow. In other forms of the invention the gas or air flow path vents directly to the environment. In the various embodiments, an enlargement is provided in the liquid conduit or auxiliary flow path at the air separation side into which the liquid rises. The dwell time afforded by the enlargement enhances air separation. The air escapes upward while the liquid flows downward from the enlargement on its way to the artificial organ.

BRIEF FIGURE DESCRIPTION

In order that the invention may be clearly understood, it will now be described, by way of example, with reference to the accompanying drawings, wherein:

FIG. 2a is a diagrammatic view of the gas separating unit of FIG. 2 coupled to a dialyzer for dialysate degassing;

FIG. 3a is a sectional view of the preferred configuration for the conduit section of FIG. 3;

FIG. 4 is a diagrammatic sectional view of another air and gas separator according to the invention suited for coupling into the liquid inflow conduit; and FIG. 5 is a fragmentary sectional view of the top of a hollow fiber dialyzer showing additional air separating embodiments of the invention.

DETAILED DESCRIPTION OF PREFERRED EXAMPLE EMBODIMENTS AND OF THE BEST MODE OF THE INVENTION

Figure 1:
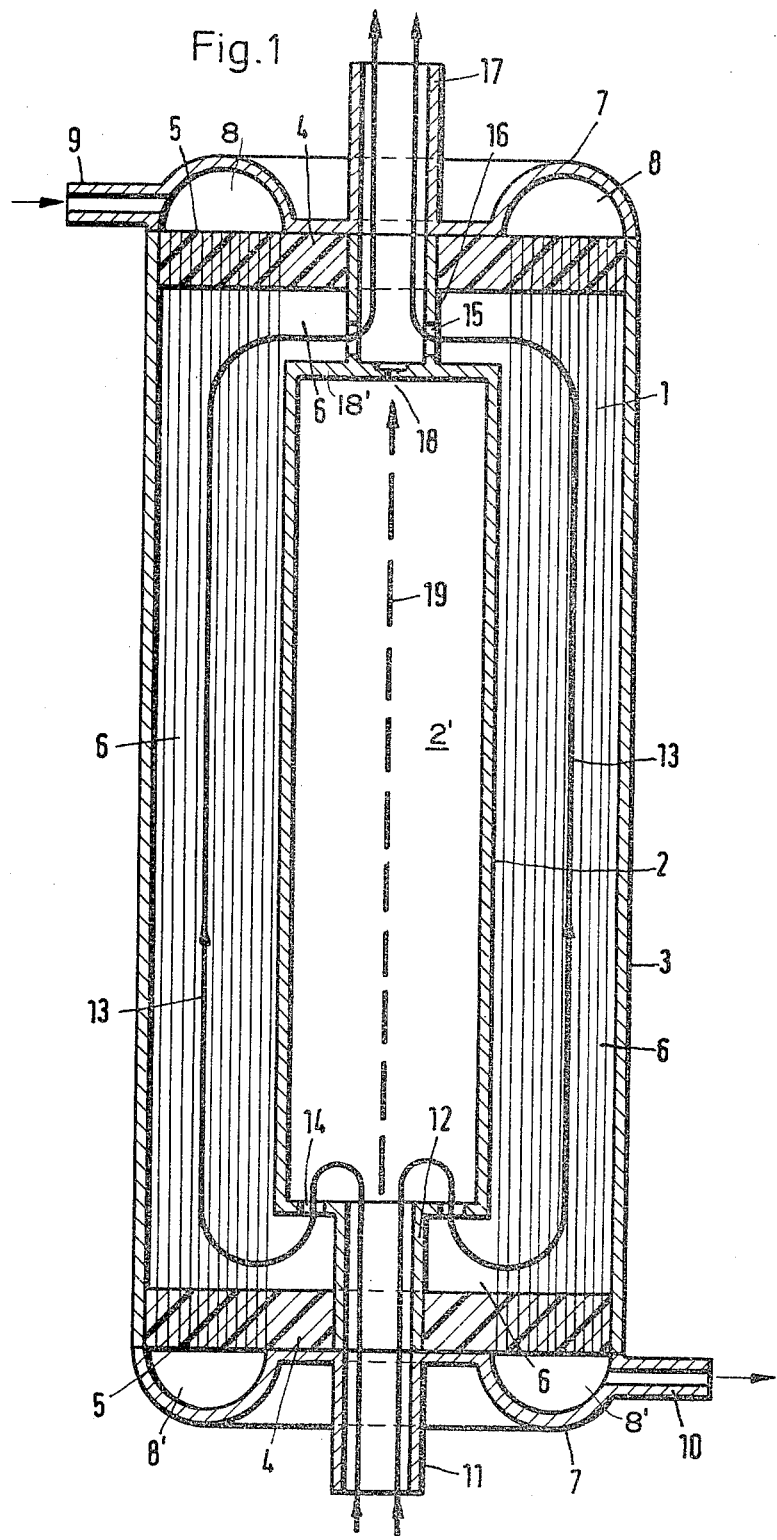
FIG. 1 is a schematic axial sectional view of an example embodiment of a hollow fiber dialyzer incorporating as an integral element, the air separating auxiliary flow path according to the invention.

FIG. 1 shows an example embodiment of a hollow fiber dialyzer equipped with a gas bypass according to the invention. The hollow fibers 1 are arranged around a core 2 which defines a central volume air trap 2'. The core 2 is mounted in a housing 3 and the blood flows through the hollow fibers 1. The hollow fibers 1 are held and sealed together at their ends by a curable, hardening material, for example polyurethane resin. Part of the cured resin is cut off in a direction perpendicular to the longitudinal axis of the dialyzer so that along the cut surface 5 the fiber ends are open. The outer surfaces, however, are sealed together at the ends toward the space 6 through which the dialysate flows. The housing 3, bundle of fibers 1, and interstices 6 form an annular configuration exchange zone surrounding the coaxial core 2 and central space 2'.

Each end of the dialyzer is equipped with a flange 7 forming a blood distribution space in operative contact with the open end surface area 5 of the hollow fibers 1. The blood enters through an inlet 9 into the upper distribution space 8 and thus into the hollow fibers 1 through which the blood flows downwardly into the lower distribution space 8'. The blood is withdrawn from the lower distribution space 8' through an outlet member 10.

The dialysate is introduced into the dialysate space 6 in the housing and between the hollow fibers 1 through an inlet member 11 which is sealed off from the blood distribution space 8' and leads upward through a pipe section 12 into the space 2' of the hollow core 2. The path 13 of the dialysate then turns downward through holes 14 in the bottom of the hollow core 2 into the interstices 6 between fibers 1 where the dialysate envelopes the outer surface of the hollow fibers. The dialysate continues its flow through hole 15 in a pipe section 16 also sealed off from the upper distribution space 8 and connected to an outlet 17 for the dialysate. Such dialyzers are further described, for example, in U.S. Pat. No. 4,141,835 assigned to the assignee of the present invention.

According to the invention the upper end wall 18' of the hollow core 2 is provided with an aperture 18 which constitutes a relatively high flow resistance to the dialysate whereby the parallel flow 19 of dialysate is negligibly small relative to the main dialysate flow 13.

In operation, if air enters through the inlet 11 with the dialysate, it will immediately rise inside the hollow core 2. The small volume of dialysate inside the aperture 18 is quickly displaced by the air whereby the latter can pass through the aperture 18 directly into the pipe section 16 and thus into the outlet 17 without contacting the fibers 1. The aperture 18 constitutes a small flow resistance for the air whereby a large airflow may pass along the parallel path 19.

In a practical embodiment according to the invention the aperture has a diameter of 0.8 mm. The proportion of dialysate flow along the path 19 measured for this example was about 5% of the entire dialysate flow. Simultaneously it was possible to prevent any air in single quantitites in amounts up to 150 milli-liters from passing into contact with the hollow fibers 1 by passing the air through the path 19 and through the aperture 18.

The flow configuration achieved by the example embodiment of FIG. 1 also facilitates bypass of air or gas around the exchange zone defined by fibers 1 and interstices 6. Dialysate liquid rises upward through liquid inlet 11 and channel or conduit 12 into the elongate central chamber or volume 2' which functions as an eddy chamber, air or gas trap, and provides dwell time for enhancing separation. The dialysate liquid, from which the air and gas is to be separated in the volume 2', exits, however, in a downward direction through the bottom openings 14. The dialysate liquid enters into the volume 2' in an upwardly directed current thereby imparting an upward flow tendency to the entrained air and gases. The liquid has some dwell time, however short in the chamber 2', before the liquid exits into the exchange zone through the holes 14 in the base of chamber 2' while air and gas continue to rise. The gas exits through aperture 18 and enters into the dialysate fluid downstream of the exchange zone. The auxiliary path of the present invention through the chamber 2' thus provides a true parallel bypass for entrained air and gases. The lower pressure in the liquid flow at outlet 17 facilitates the reentry of the separated air or gas coming from the eddy chamber volume 2', back into the used up dialysate.

A similar structure may be provided for removing air from blood. Preferably, the bypass for gas removal from blood is arranged separately so that the flow passages for the inflowing blood and for the outflowing blood may be arranged close to each other. However, the gas separator may also be incorporated in the dialyzer itself.

A feature and advantage of the example dialyzer of FIG. 1 is that the auxiliary flow path and air bypass 19 is defined by the normal internal structures of the artificial organ as described, for example, in U.S. Pat. No. 4,141,835. The air separating path is thus incorporated into the internal spaces of the device and forms an integral part of the artificial organ. Thus, the air separating flow path utilizes the central coaxial space 2' defined by hollow core wall 2, part of the existing structures and internal spaces of the artificial organ.

Furthermore, the auxiliary flow path elements define a liquid flow path through inlet 12 and through the holes 14 which is in series with the intersticeal spaces 6 upstream of the exchange zone. The air or gas flow path 19 is connected in parallel with space 6 through inlet 12, and flow impedance 18 and outlet 17.

Figure 2:
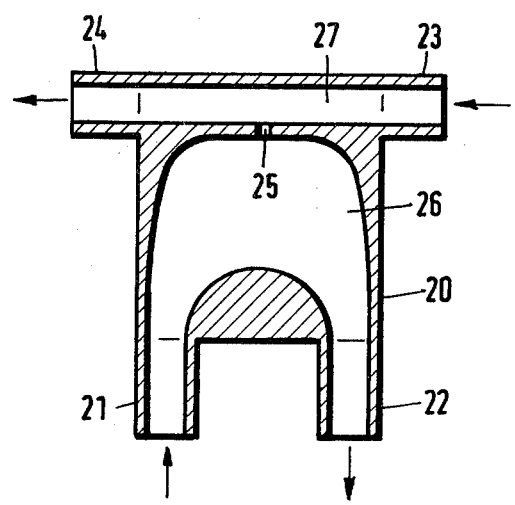
FIG. 2 is a sectional view through another practical embodiment according to the invention showing a coupling member for incorporation into liquid inflow and outflow conduits.

FIG. 2 shows an example embodiment of a gas separator not forming an integral component of the artificial organ. The embodiment of FIG. 2 is particularly useful for degassing the blood, and comprises a coupling member 20 for the blood hose members. The coupling member 20 includes two flow channels 26 and 27. The blood which is supposed to enter into the dialyzer, for example, through the inlet 9 in FIG. 1, enters the coupling member 20 through an inlet member 21 and into the space 26 whence it flows through the outlet 22 into the dialyzer. The blood exiting from the outlet 10 of the dialyzer in FIG. 1 enters into the inlet 23 and into the space 27. The blood leaves the space 27 through the outlet 24. The two spaces 26 and 27 are integrated into the liquid flow inlet and outlet conduits providing a common wall 30 between them. The inflow and outflow conduits leading to and from the artificial organ are interconnected or coupled across common wall 30, for example, by a small aperture 25 which permits air or gas exchange by a flow of air from the domed space 26 into the space 27 without any substantial flow resistance. However, only a small quantity of blood may pass through the aperture 25 which constitutes a large flow resistance to the incoming blood or rather to the blood flow in the blood supply conduit connected to the inlet 21. Hence air in the blood conduit has a chance to pass directly into the blood discharge conduit or space 27. The domed space 26 constitutes an eddy chamber air trap affording dwell time for the liquid during which separation is enhanced. If the device of FIG. 1 is combined with that of FIG. 2 gas may be removed from blood that is being dialyzedas well as from the dialysate.

The gas separating unit 20 according to the example embodiment of FIG. 2 contrasts with the example of FIG. 1 in providing an air bypass directly from the inflowing conduit to the outflowing conduit around the entire artificial organ outside of the organ. This is accomplished, however, by a combination or integration of the inflow and outflow conduits across a common wall and by a device which itself becomes an integral part of the conduits. The inlet channel is below the common wall 30 while the outlet channel is above so that gas and air may rise through the differentially or selectively permeable area 25. The inflow channel 21/22 is preferably formed in a domed upward bend or configuration with an eddy space or widening 26 at the turn to facilitate separation of air from the blood.

Gas separating unit 20 may also be used to degas the dialysate either alone or in combination with the arrangement of FIG. 1. A connection for dialysate degassing is shown in FIG. 2a. Inflow conduit 32 is coupled between the outlet 22 of the separator 20 and the inlet 33 of the dialyzer 34 while outflow conduit 35 is coupled between the inlet port 23 of the separator 20 and outlet 36 of dialyzer 34.

Figure 3:
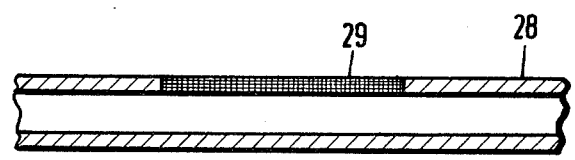
FIG. 3 is a sectional view through a third embodiment according to the invention in the form of a conduit section provided with a gas escape window as an integral part of the conduit.

FIG. 3 illustrates an embodiment of the invention in which a liquid conduit 28, for example for blood, is provided with a so-called "air-window" 29 made of a hydrophobic filter material which passes air but prevents blood from passing through the "air window" or filter 29. Thus, air may be directly eliminated to the environment. In this example embodiment the operative air separating bypass filter 29 is incorporated as an integral portion of the conduit wall itself. In the preferred arrangement the conduit also acts as an air trap when the filter 29 is arranged as a domed portion of the conduit 28 as shown in FIG. 3a. The enlargement 31 into which the blood or other liquid rises introduces a "dwell time" which enhances air separation. Thus, any air that might have possibly entered into the blood conduits may be removed again.

The arrangement of FIG. 3 may also be realized in many different ways. For example, the filter 29 may for a porous hose section whereby the conduit 28 functions as a filter or window along an entire section of its length. Further, the filter 29 may form part of a chamber, having for example a larger diameter than the hose 28 itself and so forth. In these embodiments in which the filter 29 is a hydrophobic porous filter care will be taken, to keep the size of the pores small enough so that air or gas may exit outwardly through the filter while simultaneously functioning as a sterile filter. In other words, the pores must be small enough to prevent the entry of germs into the blood stream. Thus, the pores will normally be smaller than 45 microns.

Yet another example embodiment for separating entrained air from flowing liquid is shown in FIG. 4. This air trap device 40 is coupled or integrated into the inflowing conduit and may be used alone or in combination with the devices described above. The separator device comprises an elongated gas trap or chamber 41 with vertical orientation in the operative position. The chamber introduces residence time for the liquid between inlet and outlet during which separation occurs. The inlet channel or conduit 42 delivers liquid in an upward direction into the chamber 41. An outlet channel 43 extends into the gas trap chamber from above with an opening 44 near the bottom 45 of the chamber. The outflow pipe or channel 43 is offset relative to the portion of the inflow channel to permit entrained air and gas to rise in the chamber 41. The opening 44 at the base of the trap 40 substantially restricts entry of liquid into the outflow channel to liquid at the base of the air trap. A portion 48 of the upper wall 46 of the trap is formed of a filter or gas permeable material having a high flow inpedance for liquids and a low gas flow impedance. Portion 48 may comprise, for example, a hydrophobic filter. Gases entrained in liquid delivered through inflow conduit 42 with an upward impetus, rise unimpeded toward the top of the gas trap and escape through permeable wall portion 48 while liquid is constrained to flow out the opening 44 and channel 43.

The above described examples made reference to dialyzers. However, the invention may equally be realized in connection with a hemofilter or a hemoperfusion cartridge as well as any other artificial organs and extracorporal circulatory systems such as that of an artificial heart or of an oxygenator and so forth.

From the above description of FIG. 1 it will be appreciated that the invention takes advantage of the space in the hollow core of a dialyzer which as such is known. The provision of the aperture 18 is rather expedient and economical and hardly increases the production cost of these dialyzers while at the same time greatly improving their efficiency by providing the air bypass through this hollow space 2′. However, the invention is not limited to a dialyzer having a hollow space core. A parallel bypass, such as 19, may be provided in any type of dialyzer and in such position that it bypasses the membrane arrangement as long as the bypass comprises at a suitable location a flow resistance which is larger for one medium than for the other. In an alternative embodiment the dialysate may pass through a coupling member as shown in FIG. 2. In any event, the invention may be realized in many and various modifications without departing from the basic teaching.

As mentioned, the blood stream or flow passage itself may be provided with a gas separator directly in the dialyzer structure. Thus, for example, the inlet 9 in FIG. 1 could be provided with a filter 29 as shown in FIG. 3. Instead of using in a separate structure a coupling member 20, it would be possible to connect the two blood conduits to each other, for example, by means of an adhesive to interconnect the blood conduits by one or more apertures as shown at 25 in FIG. 2. A filter of the type shown in FIG. 3 at 29 could also be used instead of the aperture 25 either in conjunction with a chamber 26 or without such a chamber. The use of a hydrophobic filter 29 has the advantage that a passage of liquid through the filter may be maintained substantially at zero by keeping the pore sizes sufficiently small as mentioned above. Porous TEFLON or polyethylene have been found to be suitable for realizing a filter such as shown at 29 in FIG. 3. Such filter may be connected in series with the artificial organ.

In the light of the above disclosure it will be appreciated that the invention may be realized as a bypass to the dialysate flow path and/or as a bypass to the blood flow path and various means may be used to provide said flow resistance in the form of a channel, an aperture, or in the form of an eddy chamber, or even in the form of a hydrophobic filter whereby these elements may be arranged to provide a bypassing connection from the inflow to the outflow or directly to the environment.

Furthermore, the elements of the invention may be used alone or in various combinations as shown in the example of FIG. 5. FIG. 5 illustrates the upper portion of a hollow fiber dialyzer of the kind described with reference to FIG. 1. Corresponding elements are identified by the same reference numerals as in FIG. 1. In addition to the auxiliary air separating flow path 19 provided for degassing the dialysate flow, the example embodiment of FIG. 5 incorporates two separating means which may be used alone or in combination for deaerating the blood.

The first air separating and removal element 50 is incorporated as an integral portion of the upper wall of inlet conduit 9 where blood enters the distribution space 8 over the face 5 of the annular bundle of open ended fibers 1. Thus, air separating element 50 is of the type shown in FIG. 3 and preferably would be located at a bend in the conduit as shown in FIG. 3a. Element 50 may be formed by hydrophobic filter material.

The second air separating and removing element 52 is formed over the ring chamber blood distribution space 8 at the top of the dialyzer, where it is incorporated as an integral part of the end housing cover or flange 7. The flange cover 7 in combination with the end face 5 of the open ended, annular fiber bundle defines the ring chamber space 8 in which blood is distributed. According to the invention this housing cover or flange 7 is curved or tapered over the space 8 with a line or region of greatest height over the face of the fiber bundle. The air separating element 52 is formed by selectively gas permeable material such as hydrophobic filter material incorporated into the housing end cover or flange 7 in this region of greatest height over the fiber bundle. By this arrangement an air trap is formed over the ring chamber blood distribution space 8 for selective removal and venting of air to the environment through the separating element 52. It can be appreciated that the dialyzer of this embodiment of the invention is normally operated with the longitudinal axis vertically oriented.

Although the invention has been described with reference to specific example embodiments, it will be appreciated, that it is intended to cover all modifications and equivalents within the scope of the appended claims.

What is claimed is:

1. A separator for removing gas from a liquid flow before the liquid flow passes into and through an artificial organ and for returning removed gas back into the liquid flow after the liquid flow has passed from an inlet to an outlet of the artificial organ, comprising inflow channel means (20) for coupling to an inlet of the artificial organ; outflow channel means (27) for coupling to an outlet of the artificial organ, said outflow channel means (27) being positioned over and adjacent to the inflow channel means (20) in its operative position; common wall means (30) joining the inflow channel means (20) and the outflow channel means (27), said common wall means comprising flow resistance means (25) having a low flow impedance for gases and high flow impedance for liquids, said flow resistance means (25) being connectable in parallel to the artificial organ, whereby gases may pass directly from inflowing liquid back into liquid flowing out of the aritificial organ, thereby passing the artificial organ, said inflow channel means (20) being connectable in series with each other through the artificial organ for generating a pressure drop in said outflow channel means (27) relative to said inflow channel means (20) by liquid flowing out of the artificial organ and through the outflow channel means (27), said pressure drop supporting the withdrawal of gas through said flow resistance means (25) to prevent the entry of gas into an artificial organ.

2. The separator of claim 1, wherein said inflow channel means is formed to comprise a bend having a domed upward configuration in its operative position, said common wall joining the inflow and outflow channel means along the portion of said domed upward configuration.

3. The separator of claim 2, wherein said inflow channel means is enlarged in the region of said domed upward configuration to form an eddy space and gas trap which provides a dwell time for liquid in the inflow channel, and wherein gas rises to the top of said domed upward configuration for passage through the flow resistance means of the common wall means into the outflow channel means, whereby gases in the inflowing liquid substantially bypass the artificial organ or other device and pass directly to the liquid flowing out of the device.

4. The separator of claim 1, wherein said inflow channel means is shaped to form a gas trap, said common wall means being located to form part of said gas trap, and wherein said flow resistance means is located to communicate between said gas trap and the outflow channel means.

5. The separator of claim 1, wherein said flow resistance means include a selectively gas permeable material operating as hydrophobic filter means.

6. The separator of claim 1, wherein said inflow channel means is formed with a convex upward bend and said flow resistance means comprises at least a portion of the upper wall (30) of the channel means at said bend.

7. The separator of claim 6, wherein said inflow channel means is enlarged in the region of the convex upward bend (FIG. 3, 3a) for providing a dwell time volume.

8. The separator of claim 1, further comprising an artificial organ comprising elongated housing means including outer jacket means, hollow core means (2) coaxially within the outer jacket means, said outer jacket means and said core means defining therebetween an annular space, first and second end cover means engaging the outer jacket and core at each end of the housing, follow filament means substantially occupying said annular space, said hollow filament means being bonded together at the ends and having open ends facing the respective end cover means at both ends of said housing means, said end cover means defining at each end of the housing means a ring cavity above the open ends of the hollow filament means, liquid inlet means forming said inflow channel means (11, 12) operatively connected to a lower end of said hollow core means (2) and liquid outlet means (16, 17) forming said outflow channel means operatively connected to said housing means, said artificial organ having said inlet (14) in said lower end of said core (2) substantially adjacent to said inflow channel means (11, 12), flow resistance means (18) in an upper end of said hollow core, said artificial organ having said outlet (15) located substantially adjacent to said outflow channel means at the upper end of said hollow core means, said flow resistance means (18) having a low flow impedance for gases and a high flow impedance for liquid, said pressure drop supporting the withdrawal of gas through said hollow core and returning the withdrawn gas into outflowing liquid.

9. The separator of claim 8, wherein said inflow channel means at the lower end of said hollow core means are oriented for delivering liquid generally upward into the hollow core means, said inlet (14) at the lower end being arranged for delivering said liquid generally downwardly from the hollow core means into said artificial organ, whereby gases entrained in said liquid rise upwardly through the hollow core means and substantially bypass said artificial organ.

10. The separator of claim 9, wherein said inflow chanel means is located centrally in the end of the hollow core means forming auxiliary flow path means while said inlet comprises openings (14) distributed around and radially outwardly from said inflow channel means.

11. The separator of claim 1 or 8, wherein said flow resistance means (25, 18) comprise aperture means small enough to provide a high flow resistance to liquid and a low flow resistance to gas.

* * * * *